United States Patent [19]

Grant et al.

[11] Patent Number: 5,497,228
[45] Date of Patent: Mar. 5, 1996

[54] LASER BEVEL METER

[76] Inventors: Duane E. Grant, 445 S. 68Th St., Boulder, Colo. 80303; Lawrence Viele, 235 Silver Cloud, Boulder, Colo. 80302

[21] Appl. No.: 343,100

[22] Filed: Nov. 21, 1994

[51] Int. Cl.$^6$ .................................................. G01B 11/26
[52] U.S. Cl. ................................................. 356/154; 33/1 N
[58] Field of Search .................................... 356/154, 138, 356/69; 33/1 N, 551, 553, 554

[56] References Cited

U.S. PATENT DOCUMENTS 2,500,726  3/1950  Westhaver ............................... 356/154
3,869,802  3/1975  Pirner ...................................... 33/1 N Primary Examiner—F. L. Evans

[57] ABSTRACT

In a Laser Bevel Meter for measuring the angle of a bevel on a ski edge a laser beam reflects from a mirror mounted on a magnet. The mirror-magnet assembly is coupled to the ski edge and the reflected beam is coupled through a mirror tunnel to a calibrated diffuse readout screen. And according to the invention an accurate, quickly obtained measurement of the bevel angle is obtained along the length of the ski.

9 Claims, 2 Drawing Sheets

LASER BEVEL METER

FIELD OF INVENTION

The subject matter of the present invention is a method of precisely measuring a bevel that has been ground on a ski edge during a process known as ski turning. The performance of many of today's skis depends not only on skier ability, but also on an accurately ground bevel on a ski edge. After grinding, a bevel must be measured to determine whether a correct angle resulted from the grinding. This measurement has typically been a difficult one at the required precision of ¼ degree.

BACKGROUND OF THE INVENTION

The current process for measuring a bevel angle involves a human operator, a machined flat, a light source, and a micrometer. An operator tilts tile machined flat across a bevel on a ski edge until back illumination is minimized. The flat is coupled to a micrometer, which is read and converted to a bevel angle. Sources of error in this process include determination of when back illumination is minimized and misreading of the micrometer during measurement. In addition, the process is slow and provides a non-continuous measurement of bevel angle at only one point along a ski length rather than a continuous one such as would be obtained by sliding a gage along the ski.

SUMMARY OF THE INVENTION

It would be a great advantage to provide a bevel angle measurement system which does not depend on an operator's perception of when back illumination is minimized, does not depend on an operator reading a micrometer, and which is fast while providing a continuous measurement of a bevel angle along a length.

It is an object of the present invention to provide an apparatus that generates accurate and repeatable measurements of a bevel angle of a ski edge.

It is a further object of the present invention to provide an apparatus that is compact in size and provides quick measurement and accurate tracking of a bevel edge over the entire length of a ski edge in a continuous manner.

These objects and others are achieved by providing a light source, which illuminates a reflective bevel tracking means. The light reflected from the bevel tracking means is coupled to a readout means through a mirror tunnel that lengthens a light path into a much greater distance than the shortest distance from the tracking means to tile readout means. The foregoing and other objects, features and advantages of the invention will be apparent from the following more particular description of the preferred embodiments of the invention, as illustrated in the accompanying drawings.

DETAILED DESCRIPTION OF THE DRAWING

Figure 1:
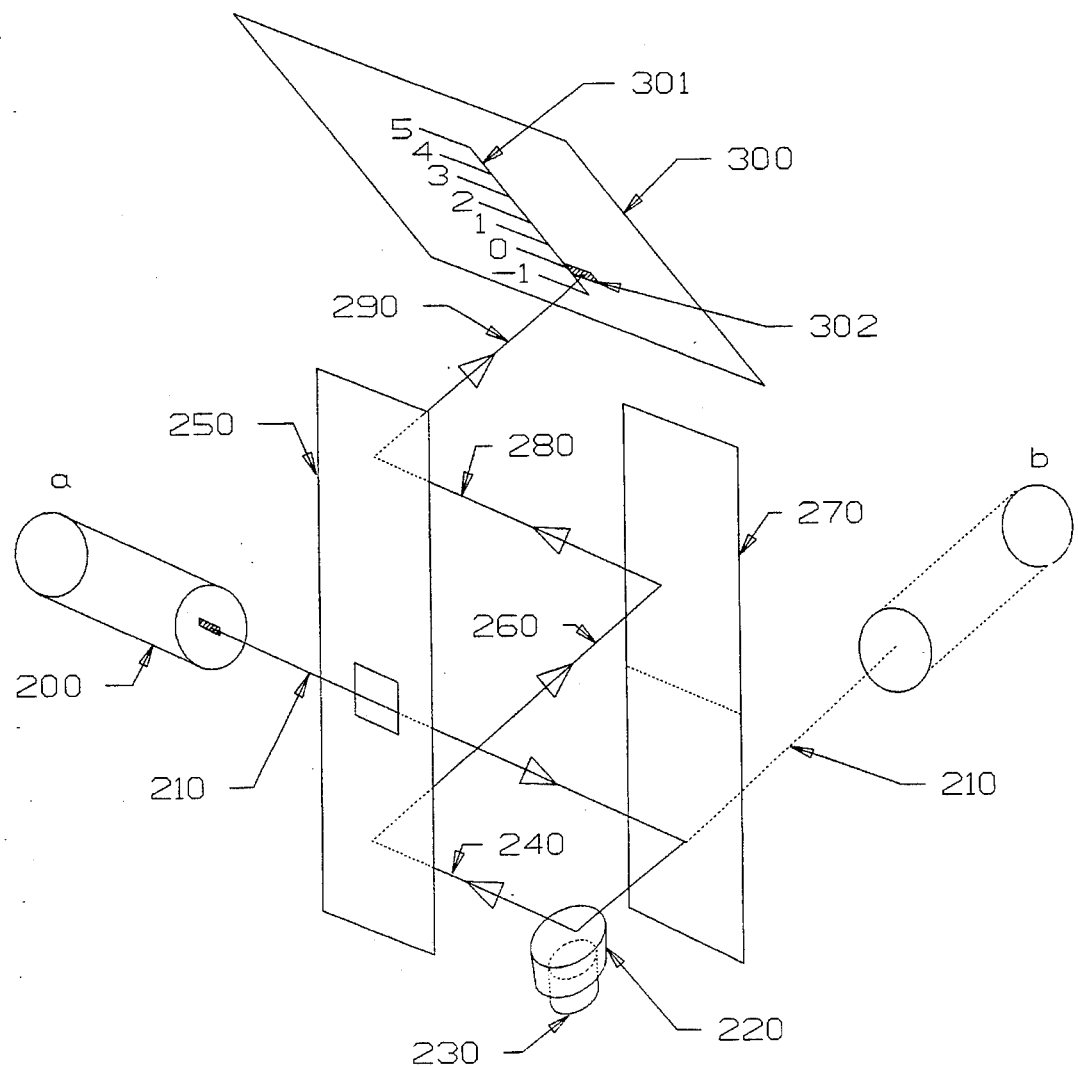
FIG. 1 shows a diagram that illustrates tile principle of the present invention.

The principle of the invention is best illustrated in FIG. 1.

A diode laser 200 located at position (a) or (b) emits a photon beam 210 that is directed toward a reflective optical surface 220 bonded to a magnet 230 that constitutes a bonded tilt assembly. Beam 210 reflects from or passes under a mirror 270. From reflective optical surface 220 a first photon beam 240 is directed toward a mirror 250. A second reflected photon beam 260 is directed toward said mirror 270. A third reflected photon beam 280 is directed to said mirror 250. Said mirrors 250 and said mirror 270 constitute a mirror tunnel. A fourth reflected photon beam 290 is directed toward diffuse screen 300 with a superimposed visual scale 301 marked in degrees. Said diffuse screen 3000 is calibrated with markings every degree; bevel angles to 0.25 degrees are estimated. A photon beam spot 302 juxtaposed at said scale 301 indicates bevel angle as said optical surface 220 bonded to magnet 230 tilts to conform to bevel angle on bottom of ski edge.

Figure 2:
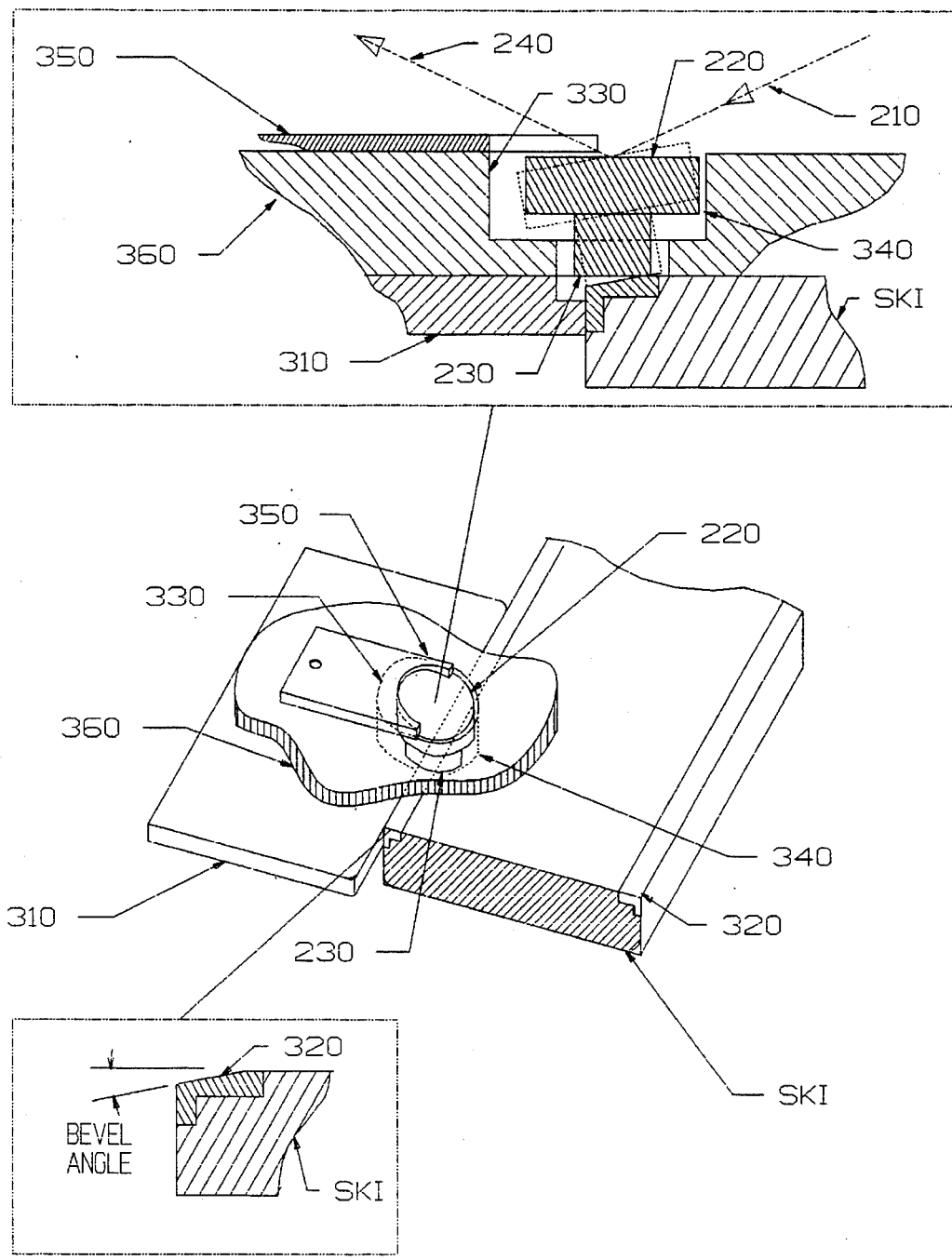
FIG. 2 shows a diagram that illustrates how a measurement from a bevel is obtained.

Method of contacting a bevel on a ski edge is best illustrated in FIG. 2.

Magnet 230 is attracted by a steel bevel edge 320 on a ski. Either a left or right ski edge can be measured. The bonded tilt assembly 220 and 230 tips angularly caused by any bevel edge 320 it contacts, and is retained in a machined elongated hole 330 in a plate 360 that becomes a captive well 340. In operation, mylar fingers 350 rest on the periphery of reflective optical surface 220 allowing an area for photon beam 210 to reflect, and mylar fingers 350 prevent bonded tilt assembly 220 and 230 from escaping from captive well 250. Elongated hole 330 allows free and easy angular movement of the bonded tilt assembly in a direction normal to a ski centerline as it moves along the bevel edge 320. Magnet 230 insures intimate contact with the ski bevel edge 320 so that the angle of reflective optical surface 220 is parallel to ski bevel edge 320. A reference guide edge 310 positions magnet 230 as it moves along ski bevel edge 320 made of a magnetic material such as steel.

Assume the angle of ski bevel edge 320 changes. Angle of the reflective optical surface 220 being coupled to bevel edge 320 through magnet 230 also changes. The change in angle of reflective optical surface 220 also results in a change in position of photon beam 290 that forms photon beam spot 302 on diffuse screen 300, since beams 240, 260, 280 and 290 are coupled to diffuse screen 300 through reflective optical surface 220 and mirrors 250 and 270. Position of beam 290 on screen 300 moves 2 degrees for every 1 degree of movement of bonded tilt assembly 220 and 230 and corresponding ground angle on ski edge for any position along bevel edge 320. A magnification of sensitivity by a factor of 2 is thereby obtained.

It will now be seen that in the configuration described, unlike the prior art, the measurement of a bevel edge can be done precisely with repeatability, because optical measurement is assured through intimate contact of bonded tile assembly 220 and 230 that is free to move while still confined to captive well 340.

While the invention has been shown and described with reference to a preferred embodiment thereof, it will be understood by those skilled in the art that changes in details may be made without departures from the spirit and scope of the invention, and the invention is therefor not to be limited except as defined in the claims.

We claim:

1. An apparatus for visual measurement of the angle on a bevel of a flat surface, comprising:

(a) a means for generating photons;

(b) a means for reflecting photons and tracking said bevel edge, which receives photons from said means for generating photons;

(c) a means for mounting said means for reflecting photons and tracking said bevel edge;

(d) a means for transmitting photons, which receives photons from said means for reflecting photons and tracking said bevel edge;

(e) a means for indicating the presence of photons with bevel angle measurement, which receives photons from said means for transmitting photons.

2. An apparatus as defined in claim 1, wherein said means for generating photons is a laser.

3. An apparatus as defined in claim 1, wherein said means for reflecting photons and tracking said bevel edge comprises a reflective surface mounted on a permanent magnet.

4. An apparatus as defined in claim 3, wherein said reflective surface is a plane mirror optical surface.

5. An apparatus as defined in claim 1, wherein said means for mounting comprises a captive well.

6. An apparatus as defined in claim 1, wherein said means for transmitting photons comprises a first reflecting surface and a second reflecting surface.

7. An apparatus as defined in claim 6, wherein said first reflecting surface is a plane mirror optical surface and said second reflecting surface is a plane mirror optical surface.

8. An apparatus as defined in claim 1, wherein said means for indicating the presence of photons is a diffuse screen with bevel angle visual measurement.

9. An apparatus for measuring the angle of a bevel edge of a flat surface comprising:

(a) a laser diode module for generating photons;

(b) a plane mirror optical surface mounted on a magnet for reflecting photons generated by said laser diode module and for tracking said bevel edge;

(c) a captive well for mounting said plane mirror optical surface mounted on a magnet;

(d) a pair of mirrors, for transmitting said photons reflected from said plane mirror optical surface mounted on a magnet;

(e) a diffuse material with bevel angle visual measurement for indicating the presence of said photons received from said pair of mirrors.

\* \* \* \* \*